United States Patent [19]

Theis et al.

[11] Patent Number: 5,128,051
[45] Date of Patent: Jul. 7, 1992

[54] METHOD FOR THE CONTROL OF BIOFOULING

[75] Inventors: Alan B. Theis, Bridgewater; Jonathan Leder, Flemington, both of N.J.

[73] Assignee: Union Carbide Chemicals & Plastics Technology Corporation, Danbury, Conn.

[21] Appl. No.: 767,810

[22] Filed: Sep. 30, 1991

[51] Int. Cl.$^5$ ............................................. C02F 1/50
[52] U.S. Cl. ........................................ 210/764; 71/67; 162/161; 422/36; 514/699
[58] Field of Search ............................ 210/764–766; 162/161; 422/15, 17, 36; 514/694, 698, 699, 705; 71/67

[56] References Cited

U.S. PATENT DOCUMENTS

| | | | |
|---|---|---|---|
| 4,297,224 | 10/1981 | Macchiarolo et al. | 210/755 |
| 4,847,304 | 7/1989 | Bruckner et al. | 514/699 |
| 4,851,449 | 7/1989 | Bruckner et al. | 514/698 |
| 4,971,999 | 11/1990 | Bruckner et al. | 210/698 |
| 5,000,918 | 3/1991 | Mebes | 210/764 |

OTHER PUBLICATIONS

Costerton et al., "Bacterial Biofilms in Relation to Internal Corrosion Monitoring and Biocide Strategies", Materials Performance pp. 49–53 (1988).
Pope et al., "Mitigation Strategies for Microbiologically Influenced Corrosion in Gas Industry Facilities", NACE Paper No. 89–192, National Association of Corrosion Engineers, Corrosion (1989).
Ruseka et al., "Biocide Testing Against Corrosion-Causing Oil-Field Bacteria Helps Control Plugging", Oil and Gas Journal, pp. 253–264 (1982).
Eager et al., "The Use of Glutaraldehyde for Microbiological Control in Waterflood Systems", Materials Performance, vol. 27, pp. 40–45 (1988).
Rehn et al., "The Antimicrobial Activity of Substituted Aromatic Aldehydes", Zbl. Bakt. Hyg., I. Abt., Orig. B172, pp. 508–519 (1981).
Eager et al., "Glutaraldehyde: Impact of Corrosion Causing Biofilms", NACE Paper No. 86–125, National Association on Corrosion Engineers (1986).
Jones et al., "The Importance of Sessile Sampling in the Monitoring of Bacterial Corrosion Problems", U.K. Corrosion 1986, Birmingham, Eng.
Haack et al., "The Evaluation of Biocide Efficacy Against Sessile Microorganisms", Dev. Inc. Micro., vol. 29, pp. 247–253 (1988).
Costerton et al., "Influence of Biofilm on Efficacy of Biocides on Corrosion-Causing Bacteria", Materials Performance, vol. 23, pp. 13–17 (1984).

Primary Examiner—Thomas Wyse
Attorney, Agent, or Firm—Joseph F. Leightner

[57] ABSTRACT

A method for controlling biofouling in aqueous environments which comprises providing ortho-phthalaldehyde to aqueous systems susceptible to biofouling. The method of the invention is particularly well suited for use in industrial cooling water systems, paper manufacture and in secondary oil recovery processes.

23 Claims, No Drawings

METHOD FOR THE CONTROL OF BIOFOULING

FIELD OF THE INVENTION

This invention relates to a method for controlling biofouling in a variety of applications including water treatment, pulp and paper manufacture and oil field water flooding. More specifically, this invention relates to a method for controlling biofouling with ortho-phthalaldehyde.

BACKGROUND OF THE INVENTION

Biofouling refers to the formation of microbial deposits or biofilms on virtually any surface submerged in an aqueous environment. In the vast majority of industrial systems, biofilms are undesirable and can result in significant damage. In cooling water systems, biofilms reduce heat transfer rates, and foul pipelines and heat exchanger tubes, resulting in significantly increased frictional resistance and higher energy requirements to pump fluids. In secondary oil recovery, which involves water flooding of the oil-containing formation, biofilms can Plug the oil-bearing formation. It is also known that severe corrosion can result from the production of acids associated with the growth of certain bacterial biofilms. These bacterial biofilms are often comprised of sulfate-reducing bacteria which grow anaerobically in water, frequently in the presence of oil and natural gases.

Biofilms can contain any type of microorganism, including algae, fungi and both aerobic and anaerobic bacteria. In addition to these microorganisms, biofilms usually contain extracellular polymeric material which protects them from predation and toxins. Because these polymers restrict permeability, microorganisms contained or attached in biofilms (sessile microorganisms) are frequently significantly more difficult to kill with chemical biocides than microbes suspended or floating in the aqueous phase (planktonic microorganisms).

A wide variety of biocides that are capable of killing planktonic microorganisms are cited in the literature; see, for example, U.S. Pat. No. 4,297,224. They include the oxidizing biocides: chlorine, bromine, chlorine dioxide, chloroisocyanurates and halogen-containing hydantoins. They also include the non-oxidizing biocides: quaternary ammonium compounds, isothiazolones, aldehydes, parabens and organo-sulfur compounds.

Traditionally, the above biocides have been employed to kill planktonic microorganisms in circulating water systems such as, for example, cooling water towers and pasteurizers. Until recently, little routine monitoring of biocidal efficacy versus sessile microorganisms had been performed. Recent studies have reported that many widely used biocides are relatively ineffective against sessile microorganisms; see, for example, Costerton et al., "Bacterial Biofilms in Relation to Internal Corrosion Monitoring and Biocide Strategies", *Materials Performance*, p. 49-53 (1988).

Only a few of the non-oxidizing biocides have been documented as being effective in killing sessile microorganisms in established biofilms. The literature has cited isothiazolones, formaldehyde and glutaraldehyde as being effective against such sessile microorganisms. Ruseska et al. report that isothiazolone was effective in controlling biofilms. "Biocide Testing Against Corrosion-Causing Oil-Field Bacteria Helps Control Plugging", *Oil and Gas Journal*, p. 253-264 (1982). Pope et al. have reported that formaldehyde performed well in one test but poorly in another test. "Mitigation Strategies for Microbiologically Influenced Corrosion in Gas Industry Facilities", NACE paper no. 89-192, National Association of Corrosion Engineers, Corrosion 1989. Glutaraldehyde was found effective in removing biofilm deposits and controlling the number of viable organisms in dynamic laboratory reactors which simulate waterflood pipeline conditions. Eagar et al., "The Use of Glutaraldehyde for Microbial Control in Waterflood Systems", *Materials Performance*, Vol. 27, p. 40-45 (1988). Problems with the currently practiced technologies include the need to use relatively high concentrations of the biocides for long contact times in order to kill the sessile microorganisms.

Accordingly, a need exists to provide a biocide which is effective against sessile microorganisms and which is capable of being employed at levels below which current biocides are employed.

SUMMARY OF THE INVENTION

The Present invention is directed to a method for controlling biofouling in an aqueous system which method comprises providing ortho-phthalaldehyde to the aqueous system in an amount at least sufficient to kill sessile microorganisms contained therein. It has been found that ortho-phthalaldehyde is particularly effective in killing sessile microorganisms present in various aqueous environments susceptible to biofouling and that it is more effective in this respect than other biocides reported in the literature.

DETAILED DESCRIPTION OF THE INVENTION

Ortho-phthalaldehyde has the formula

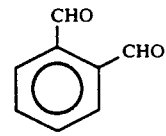

and is sometimes referred to herein for brevity as "OPA."

In practice, OPA is provided to the aqueous system in an "antimicrobially-effective amount". By this term as used herein, is meant at least the minimum amount of OPA required to substantially kill or inhibit the growth of microorganisms which adhere to the walls and other structural surfaces of the system. Also contemplated by the method of the invention is providing OPA to the aqueous system in an amount at least sufficient to inhibit regrowth or growth of such microorganisms. The particular amount of OPA required varies depending on a number of factors, including the species of sessile microorganism, the contact time between OPA and the microorganism, and the aqueous system in which OPA is employed.

Generally, OPA can be employed in the method of this invention at concentrations up to about 5 weight percent, based on the weight of water in the aqueous system to be treated. However, in view of its efficacy as a biocide against sessile microorganisms, OPA is usually used in amounts as low as from about 0.5 to about 1000 parts per million (ppm), and more usually from about 5 to about 500 ppm, by weight of water. Normally, no more than about 10 to about 250 ppm is required. If desired, concentrations of OPA exceeding about 5 weight percent (50,000 ppm), which is the limit of OPA solubility in water at 25° C., can be achieved by use of a water miscible co-solvent such as water miscible glycols, alcohols, furans and ethers. Illustrative of suitable co-solvents for use in the method of this invention are ethylene glycol, methanol, ethanol and tetrahydrofuran. Generally, when a co-solvent is used, the higher boiling co-solvents are preferred such as, in particular, ethylene glycol.

Although glutaraldehyde and formaldehyde are the preferred compounds previously disclosed in the prior art for killing or inhibiting the growth of sessile microorganisms, it has been found that OPA is more effective than either one of these other biocides in killing or inhibiting the growth of sessile microorganisms. It is to be understood, however, that OPA may be used in the method of this invention in combination with one or more of glutaraldehyde, formaldehyde and other biocides. Illustrative of such other biocides are: chlorine, bromine, chlorine dioxide, chloroisocyanurates, halogen-containing hydantoins, quaternary ammonium compounds, isothiazolones, parabens and organo-sulfur compounds.

The aqueous systems that are treated by the method of this invention are systems which are capable of sustaining the growth of sessile microorganisms. Such systems may contain a broad spectrum of sessile microorganisms including bacteria, yeasts, fungi, molds and algae. It is to be understood that the sessile microorganism-containing systems which are treated by the method of this invention may also contain, and frequently do contain, planktonic microorganisms.

Rapid kill of microorganisms is particularly important in industrial Processes in which contact between the biocide and microorganism is relatively brief. Examples of such processes include: (1) treatment of cooling water and paper mill slurries in which a portion of the water is periodically lost or removed and replaced with fresh water, so that the biocide is lost within several hours of its addition; (2) oil field water flooding in which the biocide is used in a "once-through" system; and 3) conveyor lubricants. Such systems may have contact times of less than four hours.

In addition to the speed of kill, the extent of kill in long-term contact situations is also important in many processes. Examples include (1) control of biofouling in recirculating industrial aqueous fluids such as metal working fluid or heat transfer fluid; and (2) killing microorganisms in closed loop aqueous systems such as air conditioning, air washer or chilled water systems.

The Examples which follow are presented for the purpose of illustrating the invention and are not to be construed as unduly limiting thereon. All parts and percentages are by weight unless otherwise specified.

Definitions

The following designations used in the Examples and elsewhere herein have the following meaning:
ml — milliliter(s)
mm — millimeter(s)
mMole — millimole(s)
I.D. — inside diameter
O.D. — outside diameter
g — gram(s)
oz — ounce(s)
ppm — parts per million by weight of water
GA — glutaraldehyde
FA — formaldehyde
TGE — Tryptone Glucose Extract
SRB — sulfate-reducing bacteria The following procedures were used to cultivate the various types of microorganisms used in the Examples.

DEVELOPMENT OF AEROBIC BIOFILMS ON STAINLESS STEEL PENICYLINDERS — Procedure A Approximately 20 ml of sterile Bacto TGE broth (Difco Labs) were placed in a sterile Petri dish (15 × 100 mm). To this media, 10 ml of a 24 hour culture of the aerobic organisms to be tested were added. Sterile, stainless steel penicylinders (10 mm O.D., 7 mm I.D., 10 mm long) were then placed in the inoculated media. The cylinders were placed in the dish either on-end or on-side. The Petri dish containing the cylinders was then incubated at 37° C. for 48 hours. At that time, cylinders were individually removed aseptically using forceps, blotted on sterile filter paper, and washed three times by dipping in sterile saline solution. This procedure was used to ensure that only organisms that were firmly attached in the biofilm were tested.

Two biofilm-coated cylinders were then carefully dropped into separate 10 ml test tubes containing biocide solutions of varying concentrations. After one hour and four hour contact times, a cylinder was aseptically transferred to a fresh tube of TGE broth and vortexed for 30 seconds to remove all sessile organisms. The resulting broth suspension was then serially diluted and plated using TGE agar for enumeration. Plates were incubated for 48 hours at 37° C. before counting.

DEVELOPMENT OF SULFATE-REDUCING BACTERIA BIOFILM ON MILD STEEL PENICYLINDERS — Procedure B SRB-containing media were prepared as follows:
14.5 g of Bacto Sulfate API Broth (Difco Labs) and 2.0 g Bacto Agar (Difco Labs) were added to 1000 ml distilled water. The solution was heated and stirred until all components were dissolved. A 1% solution of sodium thioglycollate in distilled water was also prepared. Both solutions were then autoclaved at 121° C. for 30 minutes. After cooling, 5 g of the sodium thioglycollate solution was added to the media mixture.

Mild steel penicylinders (10 mm O.D., 7 mm I.D., 10 mm long) were cleaned by soaking for 10 minutes in 0.5% hydrochloric acid. Cylinders were then rinsed three times with distilled water and dried before use.

A 4 oz screw-capped bottle was purged with argon to remove oxygen, capped and then autoclaved. After cooling, 100 ml of sterile SRB media was added to this bottle. Cleaned penicylinders were then added along with 10 ml of a five day old SRB culture. All operations were conducted under a constant stream of argon to minimize oxygen levels. The bottle was then incubated for 7-14 days (depending on the SRB used) at 37° C. At that time, cylinders were individually removed aseptically using forceps and blotted on sterile filter paper.

Two biofilm-coated cylinders were then carefully dropped into separate 10 ml test tubes of deaerated biocide solutions of varying concentrations. All of the biocide and control solutions contained 30 ppm of a non-ionic nonyl phenol ethoxylate surfactant (TERGITOL ® NP-4, Union Carbide Chemicals and Plastics Company Inc., Danbury, CT). After one hour and four hour contact times, a cylinder was removed, blotted on sterile filter paper, and placed into a commercially available SRB vial (C&S Laboratories, Tulsa, OK). The vial was then sonicated (Bransonic Model 12)

for 30 seconds to remove sessile organisms. The resulting solution was serially diluted into additional SRB vials for enumeration. Vials were grown for 28 days at 37° C. before reading. Blackening of the vials was used as an indication of growth.

GROWTH OF PLANKTONIC SULFATE-REDUCING BACTERIA — Procedure C

A stock culture of the SRB to be tested was grown in a commercial SRB vial for 4 days at 37° C. The vial was then purged for approximately 30 seconds with argon to remove excess hydrogen sulfide. At that time a series of SRB vials were each inoculated with 0.1 ml of this stock culture. These vials were then incubated at 37° C. for 4 days. Each of these vials was then purged with argon. Appropriate stock solutions of biocide were prepared so that additions of 0.1–1.0 ml provided the desired concentration of biocide in each SRB vial. After 1 hour and 4 hour contact times, 1 ml aliquots were removed from each vial and were injected into fresh SRB vials. These vials were then serially diluted for enumeration.

To minimize error, all biocide concentration/contact time points reported below were tested in duplicate and the results averaged. Results are reported as log reduction of microorganisms compared to control cylinders treated in the same manner except that no biocide was employed.

EXAMPLE 1

Results Versus Aerobic Bacterial Biofilms

An oil field isolate of aerobic bacteria was utilized in all aerobic biofilm experiments. This culture was taken from a water-flooded oil well in Texas and was tentatively identified as containing predominantly Pseudomonas species. The biofilms were developed following above Procedure A. Respective samples were treated with various concentrations of the biocides listed below and the number of bacteria were counted after one hour and four hours of contact. The results are:

TABLE 1

| Biocide | Conc. ppm* | log reduction after | |
|---|---|---|---|
| | | 1 hr | 4 hr |
| GA | 10 | 0.1 | 0.7 |
| GA | 25 | 0.3 | 1.7 |
| GA | 50 | 5.1 | 5.1** |
| OPA | 5 | 0.8 | 5.1 |
| OPA | 10 | 1.4 | 5.1 |
| OPA | 25 | 5.1 | 5.1 |
| FA | 250 | 2.0 | 5.1 |
| FA | 500 | 2.6 | 5.1 |
| FA | 1000 | 5.1 | 5.1 |

*All concentrations are ppm by weight active ingredient
**5.1 represents complete kill This Example demonstrates that OPA outperformed both glutaraldehyde and formaldehyde even though the latter compounds have previously been shown to be effective nonoxidizing biocides versus biofilms.

EXAMPLE 2

Results Versus Aerobic Bacterial Biofilms

Four aromatic aldehydes were compared to OPA to determine their effectiveness in killing organisms embedded in biofilms. The compounds chosen were: salicylaldehyde (SA); ortho-vanillin (OVA); 2,3-dihydroxybenzaldehyde (DHB); and 2-carboxybenzaldehyde (CB). These four compounds were reported in the literature, Rehn, D. et al., "The Antimicrobial Activity of Substituted Aromatic Aldehydes", *Zbl. Bakt. Hyg.*, I. Abt., Orig. B 172, p 508–519 (1981), as having biological properties similar to OPA versus five different planktonic microorganisms. Based upon the minimum inhibitor concentration (MIC) cited in the article and listed below in Table 2, one would expect SA, OVA and DHB to be essentially equivalent to OPA, with CB being less effective.

TABLE 2

| Biocide | MIC values in mMole %* | | | | |
|---|---|---|---|---|---|
| | S. aureus | P. aerug. | P. vulg. | K. pneum. | C. albic. |
| SA | 0.25 | 0.25 | 0.25 | 0.25 | 0.25 |
| OVA | 0.5 | 0.5 | 0.25 | 0.25 | 0.25 |
| DHB | 0.25 | 0.25 | 0.25 | 0.05 | <0.025 |
| CB | 0.5 | 2.5 | 1.0 | 2.5 | 1.0 |
| OPA | 0.25 | 0.25 | 0.25 | 0.25 | 0.25 |

*S. aureus = Staphylococcus aureaus
P. aerug. = Pseudomonas aeruginosa
P. vulg. = Proteus vulgaris
K. pneum. = Klebsiella pneumoniae
C. albic. = Candida albicans Respective samples of the five compounds were tested against the sessile microorganisms embedded in biofilms. The biofilm was comprised of a variety of microorganisms, but contained predominantly Pseudomonas species cultivated using Procedure A. The number of organisms were counted after one hour and four hours of contact. The results are as follows:

TABLE 3

| Biocide | Conc. ppm | log reduction after | |
|---|---|---|---|
| | | 1 hr | 4 hr |
| SA | 50 | 0 | 0 |
| SA | 100 | 0 | 0 |
| SA | 200 | 0.2 | 0.2 |
| OVA | 50 | 0 | 0 |
| OVA | 100 | 0 | 0 |
| OVA | 200 | 0.3 | 0.3 |
| DHB | 50 | 0 | 0 |
| DHB | 100 | 0.5 | 0 |
| DHB | 200 | 1.1 | 0.2 |
| CB | 50 | 0 | 0 |
| CB | 100 | 0 | 0.1 |
| CB | 200 | 0.6 | 0.5 |
| OPA | 50 | 2.9 | 7.4* |
| OPA | 100 | 3.4 | 7.4 |
| OPA | 200 | 6.0 | 7.4 |

*7.4 represents complete kill

This Example demonstrates the surprising effectiveness of OPA against the sessile microorganisms in the biofilms, even when the other aldehydes were used at levels four times the concentration of OPA. This result is particularly surprising in view of the Rehn et al. article referred to in this Example 2, indicating that the four other related aromatic aldehydes tested have comparable activity to OPA in killing planktonic aerobic organisms.

EXAMPLE 3

Results Versus Sessile Anaerobic Bacterial Biofilms

A SRB culture was obtained from a water-flooded oil well in Alaska. The bacteria were then cultivated on the walls of the steel penicylinders using Procedure B described above. Respective samples were then contacted with glutaraldehyde, formaldehyde or OPA for one and four hours with the following results:

TABLE 4

| Biocide | Conc. ppm | log reduction after 1 hr | 4 hr |
|---|---|---|---|
| GA | 100 | 3 | 4* |
| OPA | 10 | 3 | 4 |
| OPA | 25 | 3 | 4 |
| OPA | 50 | 4 | 4 |
| FA | 100 | <2 | <2 |
| FA | 250 | <2 | 3 |

*4 represents complete kill

As in the aerobic biofilm experiments, these data indicate that unexpectedly low concentrations of OPA (10 ppm) could completely kill all of the sessile anaerobic organisms contained in the biofilm within 4 hours. Significantly higher concentrations of either glutaraldehyde or formaldehyde were required to achieve the same level of effectiveness.

EXAMPLE 4

Results versus Planktonic Anaerobic Bacteria

The same sample of planktonic SRB as used in Example 3 was cultivated following above Procedure C. Respective samples of bacteria were treated with varying concentrations of OPA and the log reduction in the number of bacteria was recorded in each case. The test results are given below.

TABLE 5

| Biocide | Conc. ppm | log reduction after 1 hr | 4 hr |
|---|---|---|---|
| OPA | 100 | 0 | 0 |
| OPA | 250 | 1* | 1-2 |
| OPA | 500 | 2-3 | ND** |

*4 represents complete kill
**ND = not done

The improved efficacy of OPA to kill sessile microorganisms is apparent when the results of Example 3 and Example 4 are compared. The results of Table 5 (Example 4) show that a complete kill of the planktonic SRB was not achieved at OPA concentrations as high as 500 ppm. On the other hand, when used to treat sessile microorganisms as in Example 3, a complete kill occurred at OPA concentrations as low as 10-50 ppm. The results of Example 3 are surprising inasmuch as it is generally thought that planktonic cells are easier to kill than microorganisms contained in biofilms.

We claim:

1. A method for controlling growth, in an aqueous system, of microorganisms which adhere to walls and other structural surfaces of the system, which method comprises Providing to said aqueous system ortho-Phthalaldehyde in an amount at least sufficient to substantially kill said microorganisms.

2. The method of claim 1 wherein ortho-phthalaldehyde is provided to the aqueous system in an amount from about 0.5 to about 1000 ppm.

3. The method of claim 1 wherein a sufficient amount of ortho-phthalaldehyde is maintained in the aqueous system to inhibit the regrowth of said microorganisms.

4. The method of claim 1 wherein the aqueous system additionally contains planktonic microorganisms.

5. The method of claim 1 wherein the aqueous system is a recirculating cooling tower.

6. The method of claim 1 wherein the aqueous system is an oil field water flood system.

7. The method of claim 1 wherein the aqueous system is an air washer or air conditioning system.

8. The method of claim 1 wherein the aqueous system is used in the manufacture of paper.

9. The method of claim 1 wherein the aqueous system is used as a metal working fluid or heat transfer fluid.

10. The method of claim 1 wherein the aqueous system is used as a conveyor lubricant.

11. A method for controlling growth, in an aqueous system, of microorganisms which adhere to the walls and other structural surfaces of the system, which method comprises providing to said system ortho-phthalaldehyde and another biocide in an amount at least sufficient to substantially kill said microorganisms.

12. The method of claim 11 wherein the other biocide is glutaraldehyde.

13. The method of claim 11 wherein the other biocide is formaldehyde.

14. A method for controlling growth, in an aqueous system, of microorganisms which adhere to walls and other structural surfaces of the system, which method comprises providing to said aqueous system ortho-phthalaldehyde in an amount at least sufficient to inhibit growth of sessile microorganisms.

15. The method of claim 14 wherein the aqueous system is a recirculating cooling tower.

16. The method of claim 14 wherein the aqueous system is an oil field water flood system.

17. The method of claim 14 wherein the aqueous system is an air washer or air conditioning system.

18. The method of claim 14 wherein the aqueous system is used in the manufacture of paper.

19. The method of claim 14 wherein the aqueous system is used as a metal working fluid or heat transfer fluid.

20. The method of claim 14 wherein the aqueous system is used as a conveyor lubricant.

21. A method for controlling growth, in an aqueous system, of microorganisms which adhere to walls and other structural surfaces of the system, which method comprises providing to said aqueous system ortho-phthalaldehyde and another biocide in an amount at least sufficient to inhibit the growth of sessile microorganisms.

22. The method of claim 21 wherein the other biocide is glutaraldehyde.

23. The method of claim 21 wherein the other biocide is formaldehyde.

* * * * *